US009409074B2

(12) United States Patent
Han et al.

(10) Patent No.: US 9,409,074 B2
(45) Date of Patent: Aug. 9, 2016

(54) RECOMMENDING SPORTS INSTRUCTIONAL CONTENT BASED ON MOTION SENSOR DATA

(71) Applicant: Zepp Labs, Inc., Los Gatos, CA (US)

(72) Inventors: Zheng Han, Beijing (CN); Jie Xu, Beijing (CN)

(73) Assignee: Zepp Labs, Inc., Los Gatos, CA (US)

( * ) Notice: Subject to any disclaimer, the term of this patent is extended or adjusted under 35 U.S.C. 154(b) by 0 days.

(21) Appl. No.: 14/470,482

(22) Filed: Aug. 27, 2014

(65) Prior Publication Data

US 2016/0059103 A1    Mar. 3, 2016

(51) Int. Cl.
H04N 21/45 (2011.01)
A63B 69/36 (2006.01)

(52) U.S. Cl.
CPC .................................. A63B 69/36 (2013.01)

(58) Field of Classification Search
CPC .................. H04N 21/4756; H04N 21/4758
USPC ........................................ 700/91; 463/9, 40
See application file for complete search history.

(56) References Cited

U.S. PATENT DOCUMENTS

| | | | |
|---|---|---|---|
| 5,610,590 A | 3/1997 | Johnson et al. | |
| 5,819,206 A | 10/1998 | Horton et al. | |
| 6,224,493 B1 | 5/2001 | Lee et al. | |
| 7,978,081 B2 | 7/2011 | Shears et al. | |
| 8,109,816 B1 | 2/2012 | Grober | |
| 8,282,487 B2 | 10/2012 | Wilson et al. | |
| 8,337,335 B2 | 12/2012 | Dugan | |
| 8,409,024 B2 | 4/2013 | Marty et al. | |
| 8,409,025 B2 | 4/2013 | Stites et al. | |
| 8,449,402 B2 | 5/2013 | Jaekel et al. | |
| 8,523,696 B2 | 9/2013 | Kamino et al. | |
| 8,589,114 B2 | 11/2013 | Papadourakis | |
| 8,593,286 B2 | 11/2013 | Razoumov et al. | |
| 8,725,452 B2 | 5/2014 | Han | |
| 8,903,521 B2 | 12/2014 | Goree et al. | |
| 8,905,855 B2 | 12/2014 | Fitzpatrick et al. | |
| 8,941,723 B2 | 1/2015 | Bentley et al. | |

(Continued)

FOREIGN PATENT DOCUMENTS

WO    WO 2012-091516 A2    7/2012

OTHER PUBLICATIONS

Allen, R., "Wireless Sensor Architecture Uses Bluetooth Standard" Electronic Design, Aug. 7, 2000, 5 Pages, Can be retrieved from <URL:http://electronicdesign.com/communications/wireless-sensor-architecture-uses-bluetooth-standard>.

(Continued)

*Primary Examiner* — Allen Chan
(74) *Attorney, Agent, or Firm* — Fenwick & West LLP

(57) ABSTRACT

A solution is provided for recommending sports video content samples to users of a recommendation service with enhanced user experience. The recommendation service generates voting scores for sports video content samples according to a voting method, and selects from among the sports content samples according to the voting scores for the sports video content samples. The voting method is based on in part on motion data for a user's sports motion and the motion data is captured by a motion data device. The sports video content samples, e.g., golf videos, can be classified into multiple classes, e.g., golf swing power related videos, and each class is related to a different aspect of the sports motion.

30 Claims, 13 Drawing Sheets

(56) References Cited

U.S. PATENT DOCUMENTS

| | | | |
|---|---|---|---|
| 8,944,928 B2 | 2/2015 | Kaps et al. | |
| 8,956,238 B2 | 2/2015 | Boyd et al. | |
| 9,039,527 B2 | 5/2015 | Bentley et al. | |
| 2005/0032582 A1 | 2/2005 | Mahajan et al. | |
| 2005/0272516 A1 | 12/2005 | Gobush | |
| 2006/0025229 A1 | 2/2006 | Mahajan et al. | |
| 2006/0166738 A1 | 7/2006 | Eyestone et al. | |
| 2008/0085778 A1 | 4/2008 | Dugan | |
| 2009/0048044 A1 | 2/2009 | Oleson et al. | |
| 2010/0103269 A1 | 4/2010 | Wilson et al. | |
| 2010/0144414 A1 | 6/2010 | Edis et al. | |
| 2010/0323794 A1 | 12/2010 | Su | |
| 2011/0099195 A1 | 4/2011 | Patwardhan et al. | |
| 2011/0230273 A1* | 9/2011 | Niegowski | A43B 3/0005 473/199 |
| 2012/0122574 A1 | 5/2012 | Fitzpatrick et al. | |
| 2012/0277890 A1 | 11/2012 | Han | |
| 2013/0150121 A1 | 6/2013 | Jeffery et al. | |
| 2013/0162546 A1 | 6/2013 | Yeh et al. | |
| 2013/0203526 A1* | 8/2013 | Finn | G09B 19/0038 473/409 |

OTHER PUBLICATIONS

Arfwedson, H., et al., "Ericsson's Bluetooth Modules," Ericsson Review, 1999, No. 4, pp. 198-205, <URL:http://www.ericsson.com/ericsson/corpinfo/Pub.s/review/1999_04/files/19990404.pdf>.

Bishop, R., "LabVIEW 8 Student Edition," 2007, 12 pages, Pearson Prentice-Hall, Upper Saddle River, NJ.

First Annual "Better Golf Through Technology," Better Golf Through Technology Conference, Feb. 17-18, 2006, 1 page, [Archived on web.archive.org on Mar. 14, 2006] Can be Retrieved at <URL:https://web.archive.org/web/20060314063211/http:/www.bettergolfthroughtechnology.com/>.

Home Page for "Concept2: Training," 1 page, [Archived on web.archive.org on Feb. 5, 2009] Can be Retrieved at <URL:http://web.archive.org/web/20090205092657/http://concept2.com/us/training/default.asp>.

Home Page for Expresso.com, 2 pages, [Archived on web.archive.org on Apr. 29, 2009] Can be Retrieved at <URL:http://web.archive.org/web/20090426023759/http://expresso.com/products_services/index.html#>.

Honan, M., "Apple unveils iPhone," Macworld, Jan. 89, 2007, 4 Pages, can be retrieved at <URL:http://www.macworld.com/article/1054769/iphone.html>.

InvenSense, "InvenSense™ Unveils World's 1st IMU Solution for Consumer Appls" InvenSense, Apr. 6, 2010, 2 pages.

Kalia, M., et al., "Efficient Policies for Increasing Capacity in Bluetooth: An Indoor Pico-Cellular Wireless System," IBM India Research Laboratory, 2000, 5 pages.

Linx Technologies, "HP3 Series Transmitter Module Data Guide" Linx Technologies, Inc., 2008, Revised Jul. 27, 2011, 13 Pages.

Otto, C., et al., "System Architecture of a Wireless Body Area Sensor Network for Ubiquitous Health Monitoring," Journal of Mobile Multimedia, 2006, pp. 307-326, vol. 1, No. 4.

Rao, R., et al., "Demand-based Bluetooth Scheduling," Pennsylvania State University, Sep. 27, 2001, 13 pages, Can be retrieved at <URL:http://www.cse.psu.edu/~gik2/papers/Bluetooth1.doc>.

Roving Networks, "Blue Sentry RN-800S-CB Data Sheet," 2009, 1 page.

Sanders, K., "Japanese WII Price, Release Date Revealed," IGN US, Sep. 13, 2006, 1 Page, can be retrieved at <URL:http://www.ign.com/articles/2006/09/14/japanese-wii-price-release-date-revealed>.

SmartSwing, "SmartSwing Introduces Affordable Intelligent Golf Club," Press Release, Jul. 19, 2005, 2 pages, [Archived on web.archive.org on Jun. 13, 2006] Can be Retrieved at <URL:https://web.archive.org/web/20060613114451/http://www.smartswinggolf.com/site/news/pr_2006_jan_23_aus.html>.

Solid State Technology, "MEMS Enable Smart Golf Clubs," Extension Media, Jan. 6, 2005, 3 pages,[Archived on web.archive.org on Jan. 15, 2016] Can be Retrieved at <URL:https://web.archive.org/web/20160115202844/http://electroiq.com/blog/2005/01/mems-enable-smart-golf-clubs/>.

Takahashi, D., "Facebook, Twitter, Last.fm coming to Xbox Live this fall" Venture Beat, Jun. 1, 2009, 5 Pages, Can be retrieved from <URL:http://venturebeat.com/2009/06/01/facebook-coming-to-xbox-live-as-microsoft-beefs-up-other-entertainment-on-xbox-360/>.

The iClub System™ "iClub.net—Contact," Fortescue Corp. 2001-2005, 1 Page, [Archived on web.archive.org on Apr. 9, 2005] Can be Retrieved at <URL:https://web.archive.org/web/20050409111624/http://www.iclub.net/contact.html>.

The iClub System™ "iClub.net—Products," Fortescue Corp. 2001-2005, 1 Page, [Archived on web.archive.org on Jul. 10, 2005] Can be Retrieved at <URL:https://web.archive.org/web/20050710075533/http://www.iclub.net/products-iclub.html.

The iClub System™ "iClub.net—Products ICLUB$^3$," Fortescue Corp. 2001-2005, 1 Page, [Archived on web.archive.org on Apr. 14, 2005] Can be Retrieved at <URL:https://web.archive.org/web/20050414233840/http://www.iclub.net/products-iclube.html.

The iClub System™ "iClub.net—Products ICLUB (Full Swing)," Fortescue Corp. 2001-2005, 1 Page, [Archived on web.archive.org on Apr. 14, 2005] Can be Retrieved at <URL:https://web.archive.org/web/20050414233828/http://www.iclub.net/products-iclub.html.

The iClub Product Brochure, 2001-2005, 2 pages.

Tuite, D., "Motion-Sensing MEMS Gyros and Accelerometers Are Everywhere," Electronic Design, Jul., 9, 2009, 6 pages, Can be retrieved from <URL:http://electronicdesign.com/analog/motion-sensing-mems-gyros-and-accelerometers-are-everywhere>.

Webster's New College Dictionary, Definition for "Virtual Reality," (3rd ed. 2008), 3 Pages.

Webpage for zigbees.com, 4 Pages, [online] [retrieved on Mar. 14, 2016] Can be retrieved at <URL:http://www.zigbees.com/h_start.htm>.

Wheeler, A, et al., "Introduction to Engineering Experimentation," 2nd Edition, 2004, Chapter 4, 10 pages, Pearson—Prentice-Hall, Upper Saddle River, NJ.

Affidavit of Christopher Butler dated Jan. 15, 2016 regarding "Rinton Press—Publisher in Science and Technology," 6 pages, [Archived on web.archive.org on Jan. 3, 2007] Can be Retrieved at <URL:https://web.archive.org/web/20070103234656/http://rintonspress.com/journals/jmmonline.html>.

Affidavit of Christopher Butler dated Jan. 25, 2016 regarding "SmartWing Intelligent Clubs," 46 Pages, [Archived on web.archive.org on Apr. 11, 2006] Can be Retrieved at <URL:https://web.archive.org/web/20060411113841/http://www.smartswinggolf.com/site/>.

Affidavit of Christopher Butler dated Feb. 19, 2016 regarding "Concept2: Training," 5 pages, [Archived on web.archive.org on Feb. 5, 2009] Can be Retrieved at <URL:http://web.archive.org/web/20090205092657/http://concept2.com/us/training/default.asp>.

Certified File History of U.S. Pat. No. 8,905,855, Feb. 2, 2016, 709 Pages.

Certified File History of U.S. Pat. No. 8,941,723, Feb. 2, 2016, 929 Pages.

File History of U.S. Pat. No. 8,903,521, 2015, 406 pages.

Certified File History of U.S. Pat. No. 8,944,928, Feb. 2, 2016, 647 Pages.

Certified File History of U.S. Pat. No. 9,039,527, Feb. 2, 2016, 1047 Pages.

Declaration of Dr. Steven M. Nesbit, U.S. Pat. No. 8,905,855, Feb. 24, 2016, 235 Pages.

Declaration of Dr. Steven M. Nesbit, U.S. Pat. No. 8,941,723, Feb. 24, 2016, 219 Pages.

Declaration of Dr. Steven M. Nesbit, U.S. Pat. No. 8,903,521, Feb. 24, 2016, 250 Pages.

Declaration of Dr. Steven M. Nesbit, U.S. Pat. No. 8,944,928, Feb. 24, 2016, 195 Pages.

Declaration of Dr. Steven M. Nesbit, U.S. Pat. No. 9,039,527, Feb. 24, 2016, 227 Pages.

Curriculum Vitae of Dr. Steven M. Nesbit, Feb. 24, 2016, 10 pages.

Claim Limitation Reference Nos. '855 Petition, Feb. 24, 2016, 6 pages.

(56) References Cited

OTHER PUBLICATIONS

Claim Limitation Reference Nos. '723 Petition, Feb. 24, 2016, 5 pages.
Claim Limitation Reference Nos. '521 Petition, Feb. 24, 2016, 4 pages.
Claim Limitation Reference Nos. '928 Petition, Feb. 24, 2016, 3 pages.
Claim Limitation Reference Nos. '527 Petition, Feb. 24, 2016, 4 pages.
PCT international search report and written opinion for PCT/US2015/047041, Nov. 12, 2015, 9 Pages.

\* cited by examiner

RECOMMENDING SPORTS INSTRUCTIONAL CONTENT BASED ON MOTION SENSOR DATA

BACKGROUND

This invention relates generally to digital content processing and particularly to sports video content ranking and recommendation based on analysis of captured sports motions.

Motion detection and recognition of a moving object, such as a golf swing, are widely used to enhance athletes' performance. The techniques for path and stance recognition for spatial accelerated motion can be used in combination with human body actions for detection of human body actions in the field of sports. Taking golf as an example, golf is a sport that often requires good control of motions of a golf club, and an accurate analysis of the golf swing motions detected by a motion sensor can enhance golf players' performances. One way to enhance a player's sports performance is to analyze the motion data captured during game play and then to study highly relevant instructional content, e.g., videos, regarding various aspects of the player's performance.

The development of digital media content sharing and Internet social networking has enabled sports players to post, view and share instructional videos illustrating various aspects of a sport. However, it may be difficult and/or time consuming for sports players to find and select appropriate sports instructional content among a large amount of available sports instructional content of varying quality and relevance. Existing solutions of sports instructional content selection and recommendation related to sport performance enhancement face challenges to provide highly relevant sports instructional content tailored according to individual players' needs with enhanced user experiences.

SUMMARY

Embodiments of the invention provide a solution to enhance sports performance of users of a recommendation service. The recommendation service ranks sports instructional content based on motion data associated sports playing and provides highly relevant sports instructional content based the ranking to the users.

A computer-implemented method for recommending a sports video content sample related to a user's sports motion is disclosed. Embodiments of the method comprise generating voting scores for sports video content samples, golf video clips, according to a voting method, and selecting from among the sports content samples according to the voting scores for the sports video content samples. The voting method is based on in part on motion data for the user's sports motion and the motion data is captured by a motion data device. The sports video content samples, e.g., golf videos, can be classified into multiple classes, e.g., golf swing power related videos, and each class is related to a different aspect of the sports motion.

Embodiments of the method further comprise generating multiple voting scores for the sports video content samples according to multiple voting methods, generating aggregated voting scores for the sports video content samples based on combining the voting scores generated for each voting method and selecting from among the sports content samples according to the aggregated voting scores for the sports video content samples.

Another aspect provides a non-transitory computer-readable storage medium storing executable computer program instructions for recommending a sports video content sample related to a user's sports motion as described above. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the disclosed subject matter

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

System Overview

Figure 1:
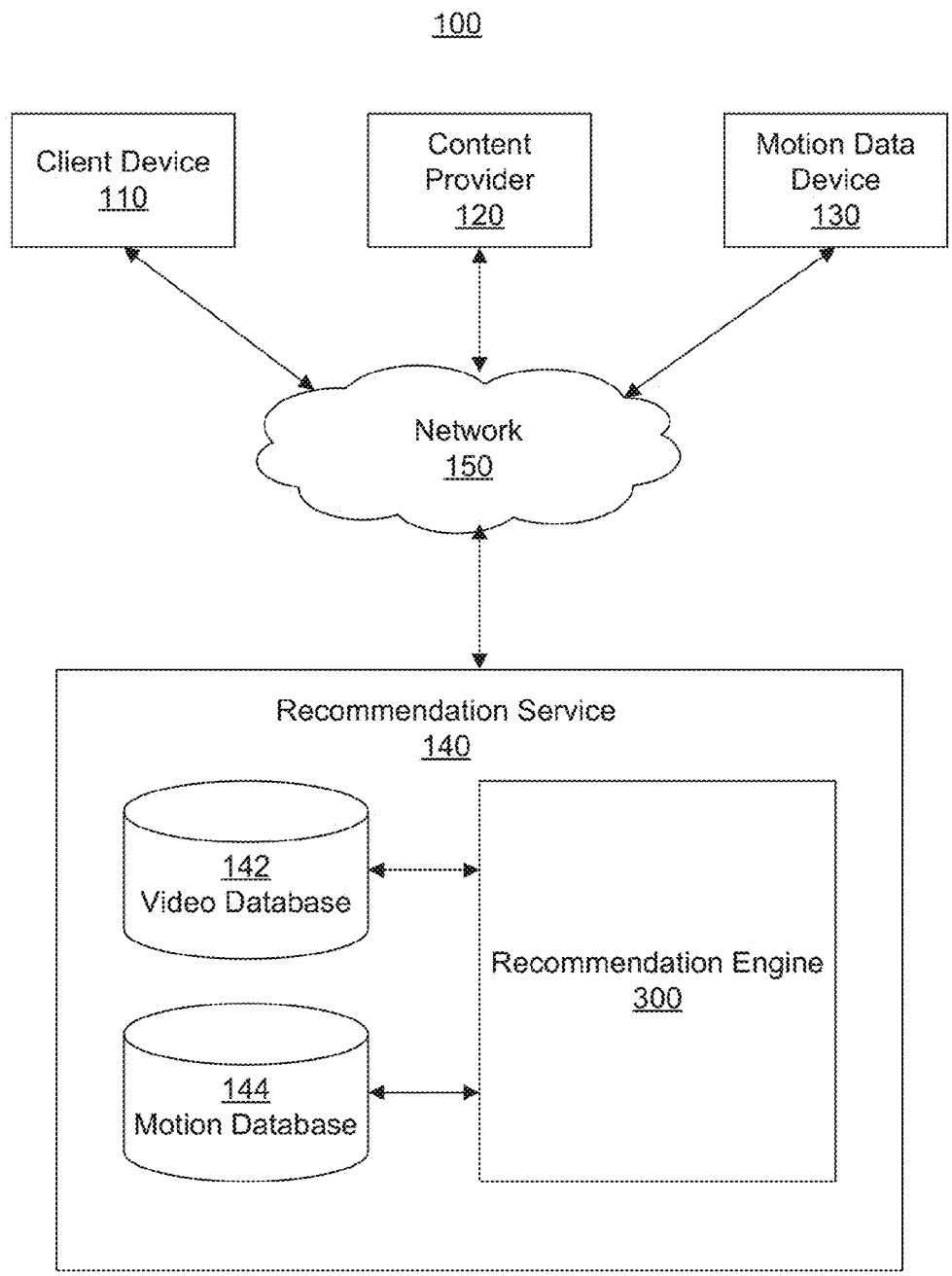
FIG. 1 is a block diagram of a computing environment for recommending sports instructional content according to one embodiment.

A solution is provided to enhance sports performance of users of a recommendation service. The recommendation service ranks sports instructional content based on motion data associated with sports playing and provides to the users highly relevant sports instructional content based on the ranking FIG. 1 is a block diagram of a computing environment 100 for recommending sports instructional content according to one embodiment. The embodiment illustrated in FIG. 1 includes a client device 110, a content provider 120, a motion data device 130 and a recommendation service 140 connected to each other by a network 150. Only one of each entity is shown in FIG. 1 in order to simplify and clarify the description. Embodiments of the computing environment 100 can have many client devices 110, content providers 120, motion data devices 130 and recommendation services 140 connected to the network 150. Likewise, the functions performed by the various entities of FIG. 1 may differ in different embodiments.

A client device 110 is an electronic device used by a user to perform functions such as consuming digital content, executing software applications, browsing websites hosted by web servers on the network 150, downloading files and the like. For example, the client device 110 may be a media streaming device, a smart phone, or a tablet, notebook, or desktop computer. The client device 110 includes and/or interfaces with a display device on which the user may view videos and other content. In addition, the client device 110 provides a user interface (UI), such as physical and/or on-screen buttons, with which the user may interact with the client device 110 to perform functions such as viewing, selecting, and consuming digital content such as sports instructional videos.

The content provider(s) 120 provides digital content of various sports to the recommendation service 140. In one embodiment, the digital content provided by the content provider 120 includes videos, digital images and text description that are designed to guide users on how to improve their sports performance in various sports, e.g., golf, baseball and tennis. Examples of golf instructional videos include videos of professional golf players playing golf, e.g., Steve Sticker, provided by Golf Channel. In one embodiment, the content provider 120 is professional broadcasters of sports events. In another embodiment, the content provider 120 is anyone who has access to a digital camera and a connection to the Internet, such as viewers of sports events. The digital content stored in a video database of the recommendation service 140 may be classified into different types, such as videos on speed, tempo, positions of sport instruments, and subtypes, such as golf videos on club speed and golf videos on hand speed.

In this disclosure, "digital content" or "digital media content" generally refers to any machine-readable and machine-storable work. Digital content can include, for example, video, audio or a combination of video and audio. Alternatively, digital content may be a still image, such as a JPEG or GIF file or a text file. For purposes of simplicity and the description of one embodiment, the digital content will be referred to as a "video," "video files," or "video items," but no limitation on the type of digital content that can be analyzed are intended by this terminology (except that they must include video). Thus, the operations described herein for analyzing and ranking video content can be applied to any type of digital content, including videos and other suitable types of digital content such as audio files (e.g. music, podcasts, audio books, and the like), documents, websites, images, multimedia presentations, and others.

The motion data device 130 captures motion data of a player during sports play. In one embodiment, the motion data device 130 is a motion sensor inserted inside a sports instrument or attached to the sport instrument, which is configured to detect motions associated with movements using the sports instrument. Each detected motion has multiple associated motion parameters. Taking a golf swing as an example, the motion parameters associated with the golf swing may include club speed, club plane, hand plane, tempo, backswing, hand speed and hips. Examples of the motion data device 130 include microelectronicmechanical systems (MEMS) sensors, electromyography (EMG) sensors and digital cameras. Examples of the embodiments of these motion sensors and motion detection and recognition systems based on motion parameters include those described in U.S. Patent Publication No. 2012/0277890 and U.S. Pat. No. 8,725,452, each of which is incorporated by reference herein in its entirety.

The network 150 enables communications among the client device 110, the content provider 120, the motion data device 130 and the recommendation service 140. In one embodiment, the network 150 comprises the Internet and uses standard communications technologies and/or protocols. In another embodiment, the entities can use custom and/or dedicated data communications technologies.

The recommendation service 140 receives sports video content provided by the content provider 120 and stores the sports video content in a video database. The recommendation service 140 also receives motion data captured by the motion data device 130 during sports play and stores the motion data in a motion database. The recommendation service 140 analyzes the sports video content and the motion data and recommends selected sports video content as sports instructional content recommendations to users based on the analysis. In one embodiment, the recommendation service 140 includes a video database 142 for storing sports video content provided by the content provider 120, a motion database 144 for storing motion data captured by the motion data device 130 and a recommendation engine 300 for ranking, selecting and providing sports instructional video content recommendations to users of the client device 110. The recommendation engine 300 is further described with reference to FIG. 3, FIG. 4 and FIG. 5 below.

Computing System Architecture

Figure 2:
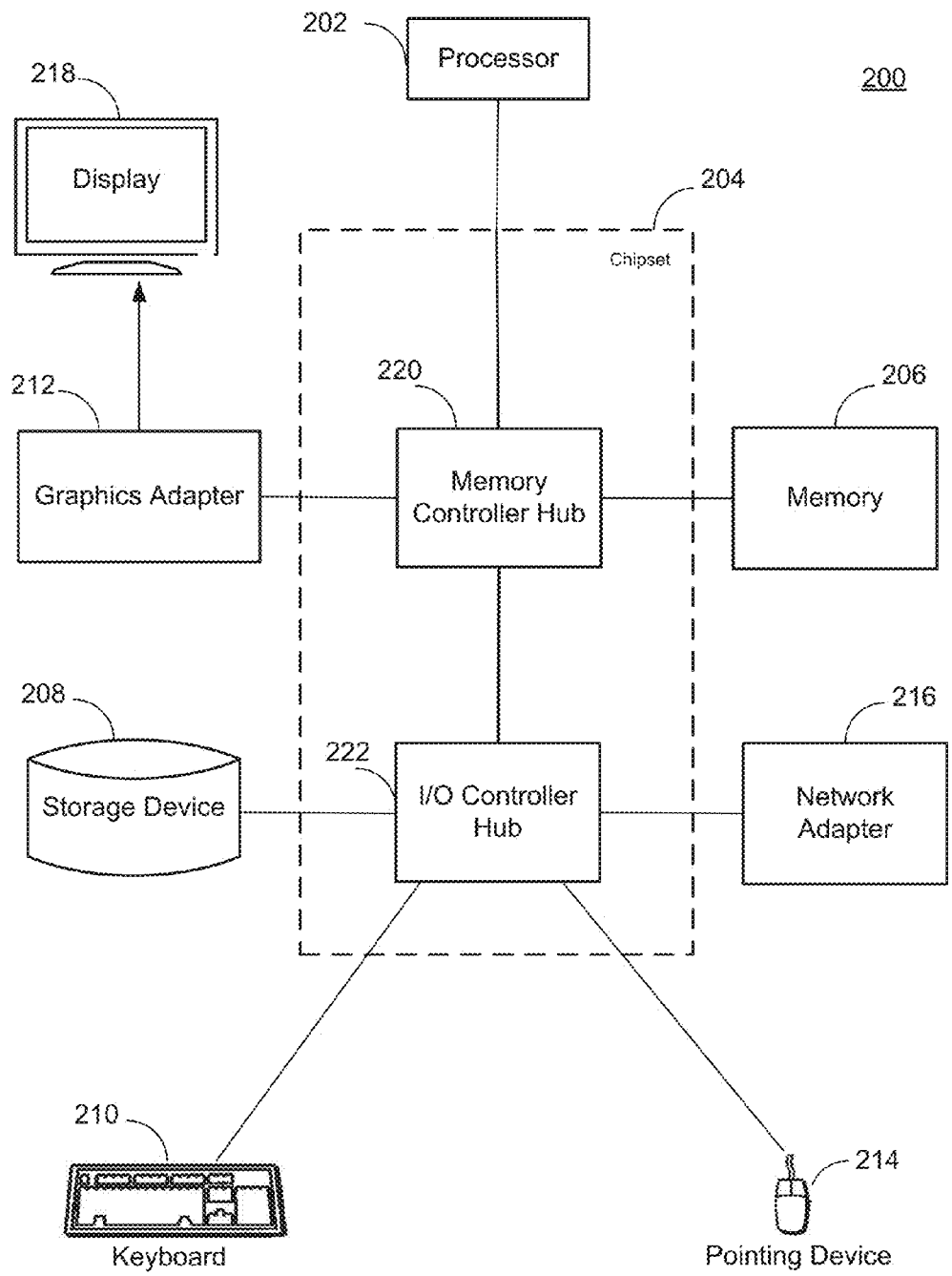
FIG. 2 is a block diagram illustrating an example of a computer for acting as a client device and/or recommendation server according to one embodiment.

The entities shown in FIG. 1 are implemented using one or more computers. FIG. 2 is a high-level block diagram of a computer 200 for acting as the content provider 120, the recommendation service 140, the motion data device 130 and/or a client device 110 according to one embodiment. Illustrated are at least one processor 202 coupled to a chipset 204. Also coupled to the chipset 204 are a memory 206, a storage device 208, a keyboard 210, a graphics adapter 212, a pointing device 214, and a network adapter 216. A display 218 is coupled to the graphics adapter 212. In one embodiment, the functionality of the chipset 204 is provided by a memory controller hub 220 and an I/O controller hub 222. In another embodiment, the memory 206 is coupled directly to the processor 202 instead of the chipset 204.

The storage device 208 is any non-transitory computer-readable storage medium, such as a hard drive, compact disk read-only memory (CD-ROM), DVD, or a solid-state memory device. The memory 206 holds instructions and data used by the processor 202. The pointing device 214 may be a mouse, track ball, or other type of pointing device, and is used in combination with the keyboard 210 to input data into the computer system 200. The graphics adapter 212 displays images and other information on the display 218. The network adapter 216 couples the computer system 200 to the network 150.

As is known in the art, a computer 200 can have different and/or other components than those shown in FIG. 2. In addition, the computer 200 can lack certain illustrated components. For example, the computers acting as the recommendation service 140 can be formed of multiple blade servers linked together into one or more distributed systems and lack components such as keyboards and displays. Moreover, the storage device 208 can be local and/or remote from the computer 200 (such as embodied within a storage area network (SAN)).

As is known in the art, the computer 200 is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device 208, loaded into the memory 206, and executed by the processor 202.

Sports Instructional Content Ranking and Recommendation

Figure 3:
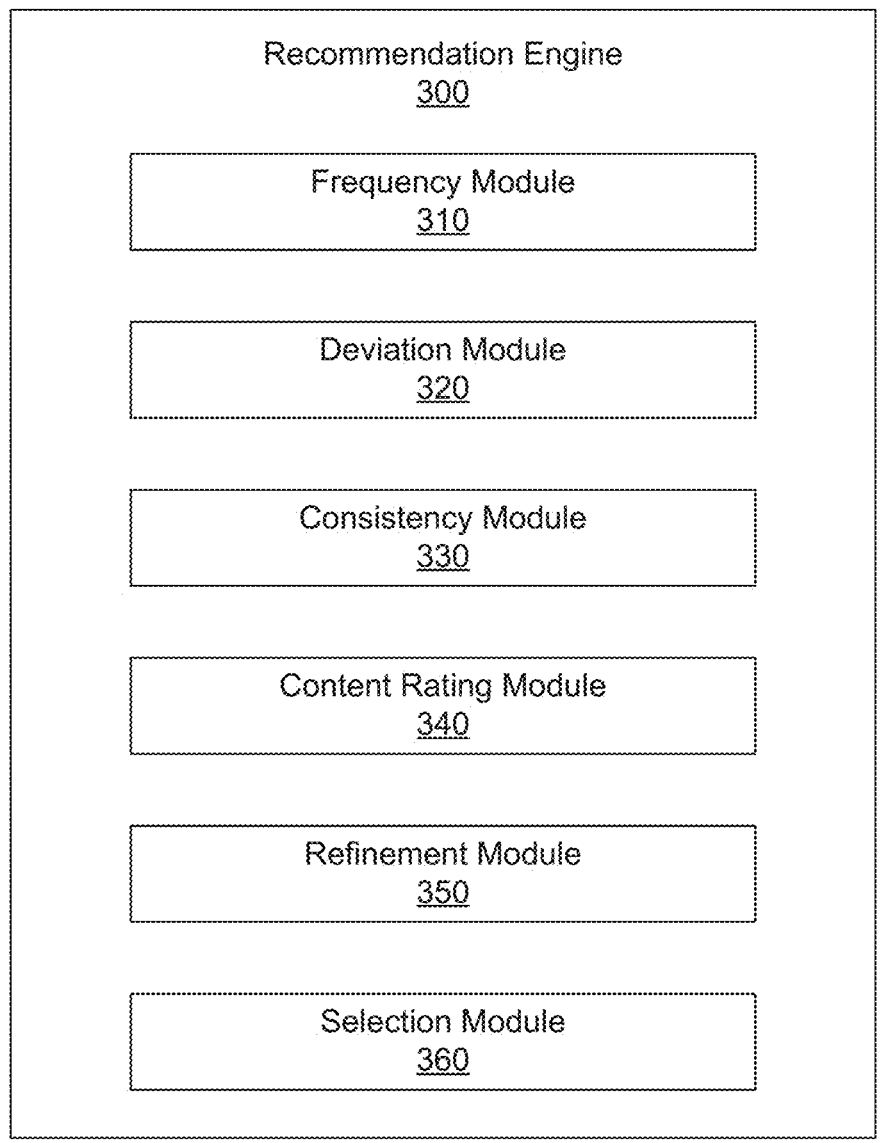
FIG. 3 is a block diagram of a sports instructional content recommendation engine according to one embodiment.

FIG. 3 is a block diagram of a sports instructional content recommendation engine 300 according to one embodiment. The recommendation engine 300 analyzes the sports video content, e.g., sports video clips from the content providers 120 stored in the video database 142, and the motion data stored in the motion database 144 and recommends sports instructional video content to users of the recommendation service 140. In one embodiment, the recommendation engine 300 ranks the video clips in the video database 142 based on the user's motion data in the motion database 144 through one or more voting processes. In each voting process, the recommendation engine 300 generates a voting score for a video clip of the sports video clips. A voting score indicates the sports performance of the player in the video clip with respect to the measurement by the corresponding voting method, some of which also take into account the user's motion data. The recommendation engine 300 selects a number of sports video clips as recommendations to the users based on the corresponding voting scores of the sports video clips.

In one approach, let parameter $\mu$ be the quantity of sports motions captured by the motion data device 130 and parameter $v$ be one motion sample out of $\mu$. Let parameter $N_{total}$ be different types of sports instructional content provided by the content provider 120. Parameter n stands for one type of sports instructional content out of $N_{total}$, and parameter $n_i$ is one content sample of the type of sports instructional content represented by parameter n. For each content sample $n_i$, the recommendation engine 300 generates a voting score $V_j(n_i)$ using a voting process of multiple voting processes j (j$\in$[0, m]), and ranks the content sample $n_i$, among all the content samples of the same type based on the voting scores of the content sample $n_i$.

Taking golf as an example, parameter $\mu$ represents a number of golf related motions, such as 1000 golf swings captured by a motion data device 130 (e.g., a motion sensor attached to a player's golf club) and parameter $v$ represents one of the 1000 golf swings. Parameter $N_{total}$ represents the number of golf videos received from the content providers 120, e.g., Golf Channel and ESPN, and the content of the golf videos can be classified into different types, such as swing power related content, swing accuracy related content and swing rhythm related content. Each video can be classified as more than one type. Parameter n represents a number of the golf videos of one classification, such as 10,000 golf videos related to swing power, and parameter $n_i$ is a video clip of the 10,000 golf videos related to swing power. The recommendation engine 300 generates a voting score for each video clip of the 10,000 golf videos related to swing power for each voting process and ranks the 10,000 golf videos based on the voting scores of the video clips.

Figure 4:
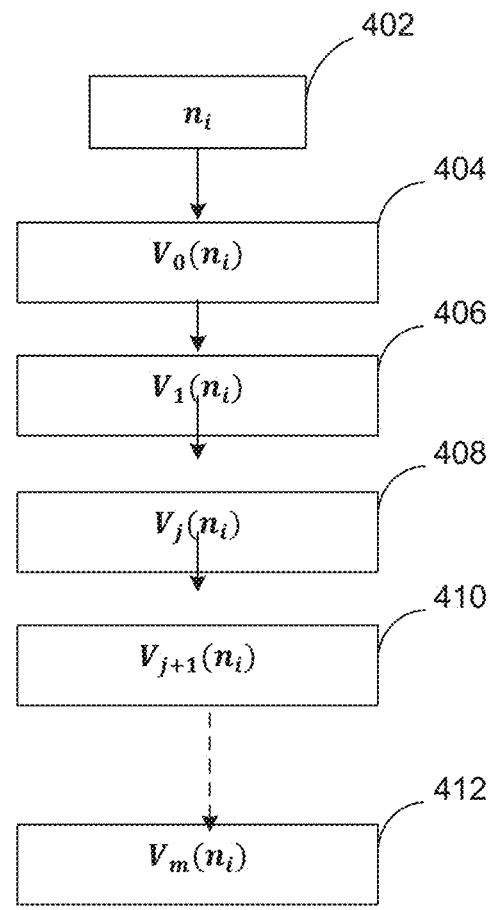
FIG. 4 is an exemplary flowchart illustrating a process of ranking sports instructional content according to one embodiment.

To further illustrate the voting processes by the recommendation engine 300 with above defined parameters, FIG. 4 is an exemplary flowchart illustrating a process of ranking a sports video content sample by the recommendation engine 300 according to one embodiment. Initially, the recommendation engine 300 receives 402 a content sample $n_i$ and generates 404 a voting score $V_0(n_i)$ using a voting method measuring how much time spent by a user of the recommendation service 140 on the content sample $n_i$, e.g., number of times that the user watched the content sample $n_i$. The recommendation engine 300 may generate 406 another voting score $V_1(n)$ based on a measurement of the differences between the content sample $n_i$ and a mean value of content samples of the same type.

At step 408, the recommendation engine 300 generates a voting score $V_j(n)$ using a voting method evaluating the consistency of content sample with respect to other content samples of the same type. At step 410, the recommendation engine generates a voting score $V_{j+1}(n)$ based on a voting method rating the content sample $n_i$ with respect to user input on the content sample.

The recommendation engine 300 may generate additional voting scores using additional and/or different voting methods. The voting methods can be independent from each other and more than one voting method can be selected by a user of the recommendation service 140 according to different applications, e.g., golf, baseball or tennis. Upon receiving the selection of voting method(s), the recommendation engine 300 generates 412 an aggregated voting score for the content sample $n_i$. In one embodiment, the recommendation engine 300 adds the voting score for each selected voting process to generate the aggregated voting score. Based on the aggregated voting scores for each content sample $n_i$, the recommendation engine 300 ranks the content samples and presents as recommendations to the users one or more content samples selected based on the ranking.

Referring back to FIG. 3, the recommendation engine 300 illustrated in FIG. 3 includes a frequency module 310, a deviation module 320, a consistency module 330, a content rating module 340, a refinement module 350 and a selection module 360. Other embodiments of the recommendation engine 300 can have different and/or additional computer modules. Likewise, the functions performed by the various entities of FIG. 3 may differ in different embodiments.

The frequency module 310 of the recommendation engine 300 generates a voting score for a content sample $n_i$ based on how much time spent by a user of the recommendation service 140 on the content sample. In one embodiment, the time that a user spends on viewing/studying video clips related to a certain type of sport content n is defined as $T_0(n)$. For each type of the sports content, the frequency module 310 computes a score $V_0(n)$ inside a score range [0, $\theta_0$] as follows using Equation 1, where $\theta_0$ is a configurable parameter for different applications of the recommendation service 140.

$$V_0(n) = \theta_0 \left\| \frac{T_0(n)}{\max(T_0(n))} \right\| (n \in N_{total}) \quad (1)$$

Initially, each content sample $n_i$ out of the total content samples n of a particular type of sports content gets the same initial score $V_0(n)$, i.e., $V_0(n_i)=V_0(n)$, where the initial score $V_0(n)$ is configurable and an example score of $V_0(n)$ for golf backswing type videos is 70.

The deviation module 320 of the recommendation engine 300 generates a voting score for a content sample $n_i$ based on a shifted standard deviation of the content sample with respect to all content samples of the same type of content n. In one embodiment, the deviation module 320 linearly shifts all content samples n such that the voting scores of the content samples have positive values. For each type of content samples n, the deviation module 320 selects a universal or a customized standard value S(n) and the average value of total sports motions μ in each type of content n as Avg(n) and calculates the deviation as follows using Equation 2.

$$\Delta(n) = \frac{Avg(n) - S(n)}{S(n)} \quad (2)$$

In one embodiment, the deviation module 320 calculates the deviation using a customized standard value S(n) based on user input. A customized standard value related to a type of sport content enables a user of the recommendation service 140 to customize his/her own goal as compared with a default value set by the recommendation engine 300. Taking golf club speed as an example, the default value set by the recommendation engine 300 is 90 mph (miles per hour), while a user of the recommendation service 140 may set his/her own goal for club speed as 95 mph or 85 mph.

Figure 12:
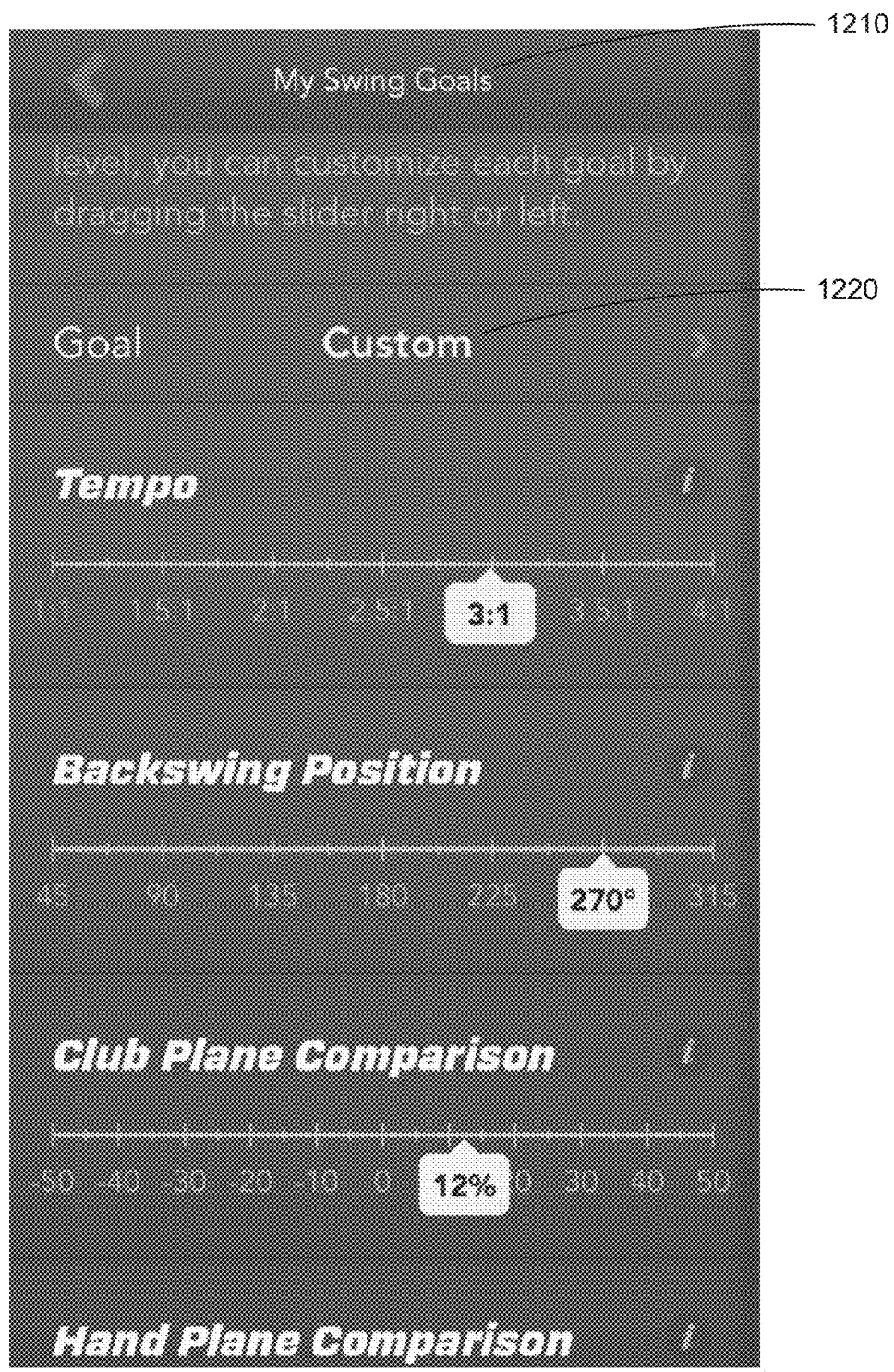
FIG. 12 illustrates a graphical user interface for users to customize their golf swinging goals.

FIG. 12 shows a graphical user interface (GUI) 1210 for users to customize their golf swinging goals on various aspects of golf swing, including tempo, backswing position and club plane comparison. The GUI 1210 includes an indication of customization 1220 and a slider for customizing each aspect of golf swing. A user may customize the values for each aspect of golf swing by sliding the corresponding slider. The GUI 1210 presents the customization by highlighting the selected values for each customization.

Returning back to the deviation module 320, the deviation module 320 generates a voting score for each type of content samples $V_1(n)$ inside a score range $[0, \theta_1]$ as follows using Equation 3, where $\theta_1$ is a configurable parameter for different applications of the recommendation service 140.

$$V_1(n) = \theta_1 \left\| \frac{|\Delta(n)|}{\max(|\Delta(n)|)} \right\| (n \in N_{total}) \quad (3)$$

In one embodiment, for each content sample $n_i$, the deviation module 320 manually tags $n_i$ with a relative factor $C(n_i)$, where $C(n_i)$ is defined as $C(n_i) \in [0,1]$. The deviation module 320 adjusts the voting score for $n_i$ as follows using Equation 4.

$$V_1(n_i) = C(n_i) V_1(n) \quad (4)$$

In one embodiment, the parameter $C(n_i)$ is a 0%-100% factor that indicate whether a content sample $n_i$ is suitable if the $\Delta(n)$ in a certain range. For example, in the content samples related to golf backswing position, some content samples are highly relevant on how to improve a user current performance related to golf backswing position by reducing the backswing position from 300 degrees to 270 degrees; some other content samples are highly relevant on how to increase the user's backswing position from 240 degrees to 270 degrees. The value of 270-degree is an example standard value represented by parameter S(n) used in Equation 2 above.

The consistency module 330 measures consistency of a content sample relative to other content samples of the same type. For example, the consistency module 330 checks how stable a particular golf swing is with respect to other 100 golf swings. In one embodiment, the consistency module 330 measures the consistency of a content sample by calculating standard variance of total sports motions μ among each type of content samples n as v(n). The consistency module 330 calculates a voting score for each type of content samples as $V_2(n)$ inside a score range $[0, \theta_2]$ as follows using Equation 5, where $\theta_2$ is a configurable parameter for different applications of the recommendation service 140.

$$V_2(n) = \theta_2 \left\| \frac{sv(n)}{\max(sv(n))} \right\| (n \in N_{total}) \quad (5)$$

$$V_2(n_i) = V_2(n)$$

The content rating module 340 generates a voting score $V_3(n_i)$ for a content sample $n_i$ based on an average rated score $R_{avg}(n_i)$ and a total rated score $R_t(n_i)$ based on user input. In one embodiment, a user of the recommendation service 140 is presented with a GUI that allows the user to rate content of a sports video, e.g., assigning a number of stars to the content. The content rating module 340 calculates the voting score $V_3(n_i)$ as follows using Equation 6, where $\theta_3^{avg}$ and $\theta_3^t$ are configurable parameters for different applications of the recommendation service 140.

$$V_3(n_i) = \theta_3^{avg} \left\| \frac{R_{avg}(n_i)}{\max(R_{avg}(n_i))} \right\| + \theta_3^t \left\| \frac{R_t(n)}{\max(R_t(n))} \right\| (n \in N_{total}) \quad (6)$$

Sometimes, the users of the recommendation service 140 may want to see different sports instructional content after each performance or session of a play, even if the motions of the multiple sessions are quite similar with each other. To enhance user experience in this situation, the refinement module 350 of the recommendation engine 300 sorts the content samples of the same type and reduces the voting scores of duplicated content samples. In one embodiment, a content queue ε lists the content samples to be sorted, and the refinement module 350 sorts the content samples of the content queue ε in terms of time, e.g., from the latest to the oldest. Given that the content queue ε has a length of δ, the refinement module 350 traverses each element of ε and generates a voting score $V_4(n_i)$ as follows using Equation 7, where $\theta_4$ is a configurable parameter for different applications of the recommendation service 140. Initially, all $V_4(n_i)$ has an initial value of 0.

$$\text{If } \varepsilon(\tau) = n_i, V_4(n_i) \mathrel{-}= \theta_4 \left\| \frac{\delta - 1 - \tau}{\delta} \right\| (\tau \in [0, \delta - 1]) \quad (7)$$

The selection module 360 generates 412 an aggregated voting score for the content sample $n_i$ upon receiving a selection of voting method(s). In one embodiment, the selection module 360 adds the voting score of the content sample $n_i$ for each selected voting process to generate the aggregated voting score as follows using Equation 8, where m represents a total number of selected voting methods.

$$P(n_i) = \Sigma_{j=0}^{m-1} V_j(n_i) \quad (8)$$

The selection module 360 generates the aggregated voting score for each content sample $n_i$ of the content samples of the same type n and ranks the content samples based on their corresponding aggregated voting scores. In one embodiment, the selection module 360 ranks the content samples from the highest voting score to the lowest voting score and selects one or more content samples as recommendations to the users of the recommendation service 140 based on the ranking. The recommendation engine 300 presents the recommendations periodically to the users, e.g., every week or every month.

In each voting process described above, the recommendation engine 300 generates a voting score for a content sample (e.g., a sports video clip) using a configurable scaling factor θ, e.g., $\theta_0$, $\theta_1$, $\theta_2$, $\theta_3^{avg}$, $\theta_3^t$ and $\theta_4$. The scaling factor θ is configurable for different applications of the recommendation service 140, e.g., golf, baseball or tennis. In one embodiment, a scaling factor represents relative importance of the corresponding voting method in the overall voting and ranking process by the recommendation engine 300. Taking golf swing as an example, the example values of these scaling factors are $\theta_0=100$, $\theta_{1=50}$, $\theta_2=50$, $\theta_3^{avg}=100$, $\theta_3^t=100$ and $\theta_4=50$.

Figure 5:
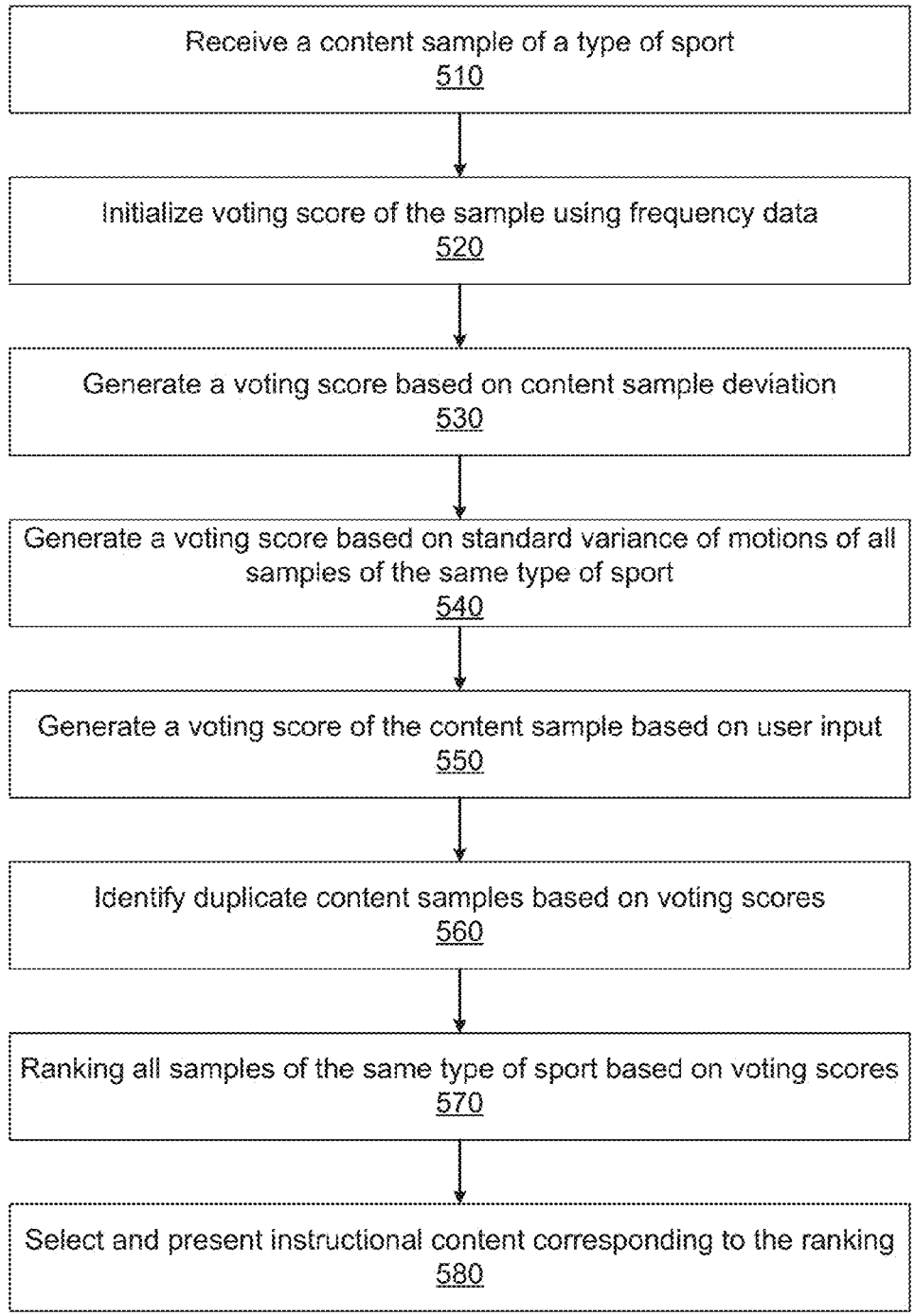
FIG. 5 illustrates steps of ranking and selecting sports instructional content according to one embodiment.

FIG. 5 illustrates steps of ranking and selecting sports instruction content by the recommendation engine 300 according to one embodiment. Initially, the recommendation engine 300 receives 510 a content sample of a type of sport, e.g., a video clip on golf backswing. The recommendation engine 300 initializes 520 the voting score of the content sample using frequency data of the content sample, e.g., how many times a user has reviewed the content sample. The recommendation engine 300 may evaluate the content sample based on how different the content sample from the average of other content samples of the same type of sports by generating 530 a voting score based on the deviation of the content sample.

The recommendation engine 300 may also consider the consistency of the content sample with respect to all types of sports video content received by the recommendation service 140. For each type of content samples, the recommendation engine 300 generates 540 a voting score based on the standard variance of the all types of sports video content. To further engage the users of the recommendation service 140, the recommendation engine 300 may evaluate the content sample based on input of an individual user or all users who rate the content sample. The recommendation engine 300 generates 550 a voting score for the content sample based on the user input.

To enable users to view different sports instructional content after each performance or session of a play without presenting duplicate content samples to the users, the recommendation engine 300 queues content samples that are to be presented to the users and sorts the content sample queues to identify 560 duplicate content samples based on augmented voting scores of the content samples. Responsive to one or more voting methods selected by a user for a type of sport, e.g., golf, the recommendation engine 300 generates an aggregated voting score for the content sample and ranks 570 the content samples of the same type of sports instructional content based on their corresponding aggregated voting scores. The recommendation engine 300 selects 580 one or more content samples based on the ranking and presents the selected content samples as recommendations to the users of the recommendation service 140.

Application of Sports Instructional Content Recommendation

The solution for recommending highly relevant sports instructional content relevant to improve sports performance of users of the recommendation service 140 described above can be applied to various types of sports. The following figures illustrate an application of the solution to playing golf. The solution described above is readily applicable to other types of sports, such as baseball and tennis.

Figure 6:
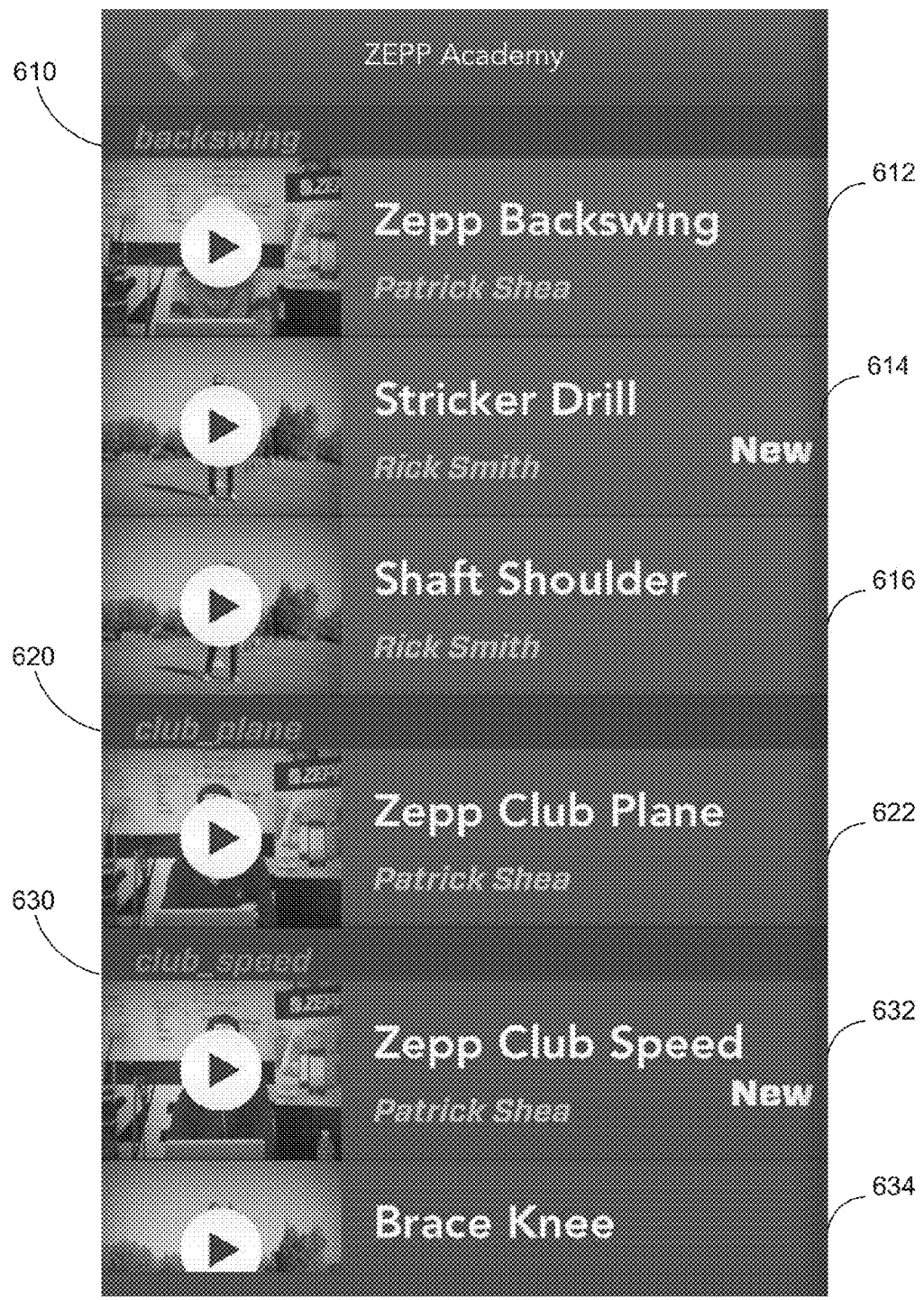
FIG. 6 shows examples of golf instructional videos for improving various aspects of golf playing performance of a player.

FIG. 6 shows examples of golf instructional videos for improving various aspects of golf playing performance of a user. The example in FIG. 6 shows that the recommendation service 140 provides instructional content in forms of videos on various aspects of playing golf. The golf videos can be provided by golf content providers, such as Golf Channel and ESPN. The types or classifications of the golf videos include backswing 610, club plane 620 and club speed 630. The backswing videos are related to a measurement of degrees of the angle of a golf club shaft between address and top of backswing. The measurement of the degrees is based on the change in the angle at the top of the backswing. At the address of the backswing, the club is at zero degree. The club plane videos are related to a measurement of the relationship between a club head of a downswing and the club head of a backswing, the corresponding distance and location of the club head at different swing positions. The club speed videos are related to a measurement of how fast a player's club head is travelling at the point the club head touches a golf ball. The recommendation service 140 can provide additional and/or different videos on other aspects of playing golf.

Under each classification of golf videos shown in FIG. 6, the recommendation service 140 further classifies the videos into subcategories. Taking backswing 610 as an example, the recommendation service 140 provides videos on subcategories of backswing, including backswings 612 illustrated by instructors selected by the operators of the recommendation service (i.e., "Zepp Backswing"), the backswings 614 illustrated by professional golfer Steve Stricker (i.e., "Stricker Drill") and the backswings 616 focusing on coordination of a player's arm and shoulder (i.e., "Shaft Shoulder").

Figure 7:
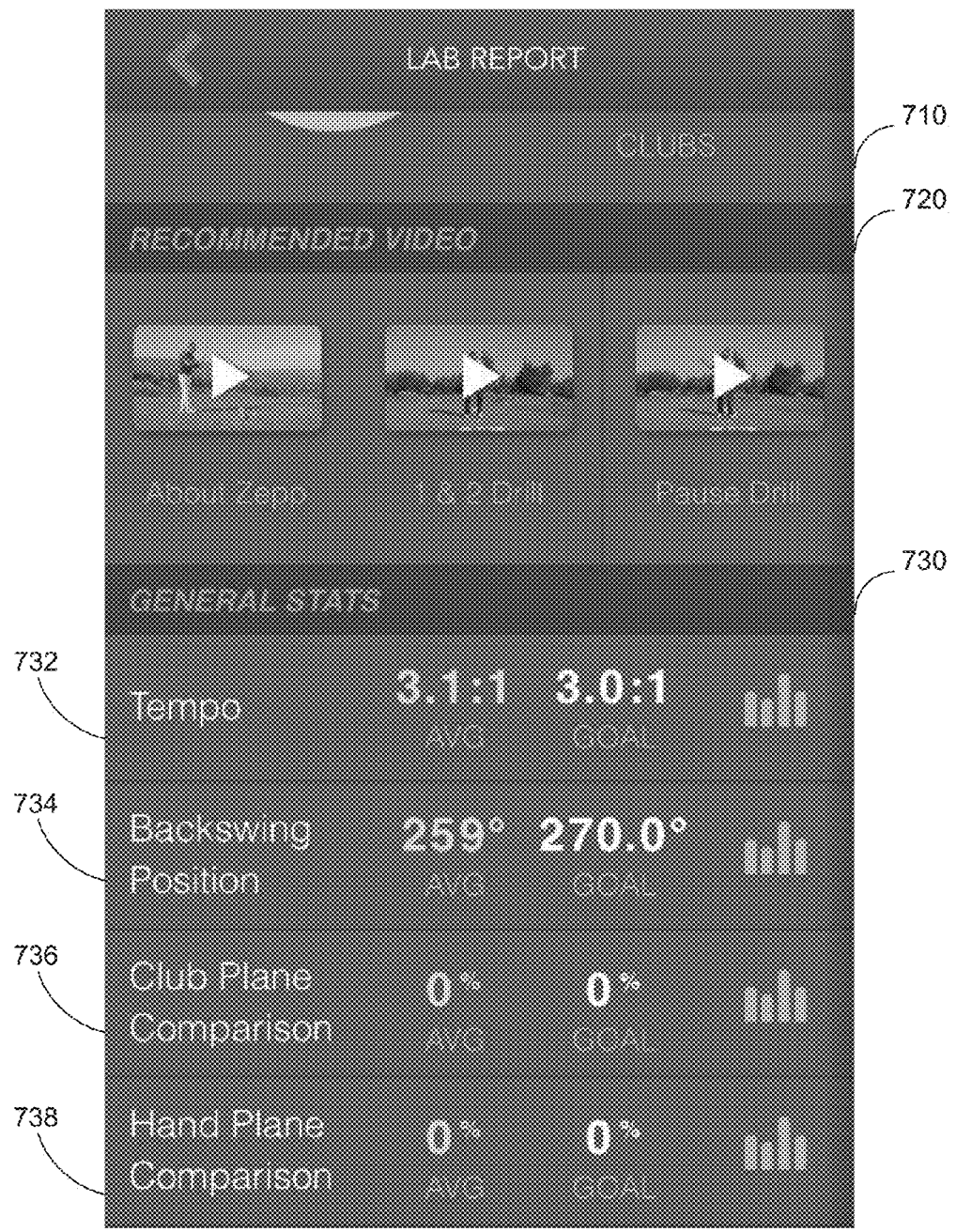
FIG. 7 shows examples of recommended videos for improving golf playing performance in terms of handling a golf club.

FIG. 7 shows examples of recommended videos 720 for improving golf playing performance in terms of handling a golf club 710. The example in FIG. 7 shows three recommended videos on golf club handling for a user based on the user's golf club handling statistics 730. In one embodiment, the user's golf club handling statistics are generated from motion parameters associated with club swings performed by the user and the club swings were captured by a motion sensor attached to the golf club used by the user. The motion parameters associated with a detected motion are collected through the motion sensor and analyzed by the recommendation service 140. Taking a golf swing as an example, the motion parameters associated with the golf swing may include, club speed, club plane, hand plane, tempo, backswing, hand speed and hips. Motion parameters related to hips measures the degrees of rotation of hips on backswing and impact of the rotation on backswing. The hand plane parameters measure the relationship between a player's hand plane of a downswing to a backswing, the relative distance and location of the downswing and the backswing. In the example shown in FIG. 7, the motion parameters related to the golf club handling include tempo 732, backswing position 734, club plane comparison and hand plane comparison. For each motion parameter shown, the recommendation service 140 also shows average performance data, target performance data (i.e., "GOAL") set by the user and a performance chart.

Figure 8:
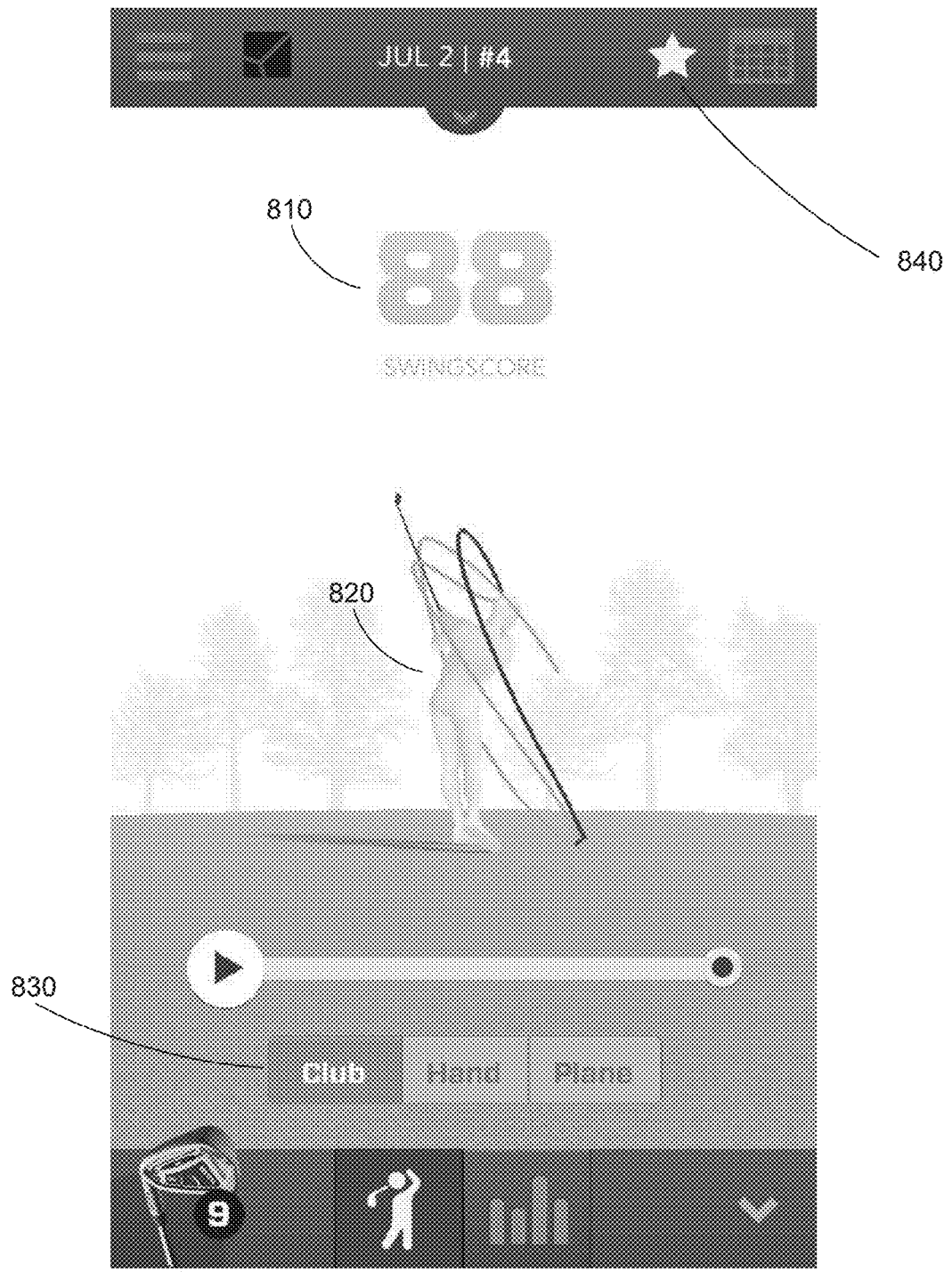
FIG. 8 shows an example of presenting golf club path aspect of a golf swing by a user of the recommendation service.

FIG. 8 shows an example of presenting golf club path aspect of a golf swing by a user of the recommendation service 140. Path and stance recognition for a spatial accelerated motion refers to detecting position and intersection angles of a moving object (e.g., a golf club swung by a player) at each time in the movement and obtaining real-time velocity of the mobbing object. In the example shown in FIG. 8, the user performance on g golf swing captured by a motion sensor has a performance score 810 (e.g., 88). The performance score on the golf swing is calculated in association with the motion parameters associated with the golf swing, e.g., club speed, club plane, hand plane, tempo, backswing, hand speed and hips. In one embodiment, the performance score on the golf swing is a weighted average score of the measurement of the associated motion parameters. The club path of the golf swing is illustrated by the curved lines 820 drawn based on the analysis of the motion parameters related to the club path 830 of the golf swing. The user performance video has a rating of 1 based on user input on the content of the video, where the rating is represented by the star 840.

Figure 9:
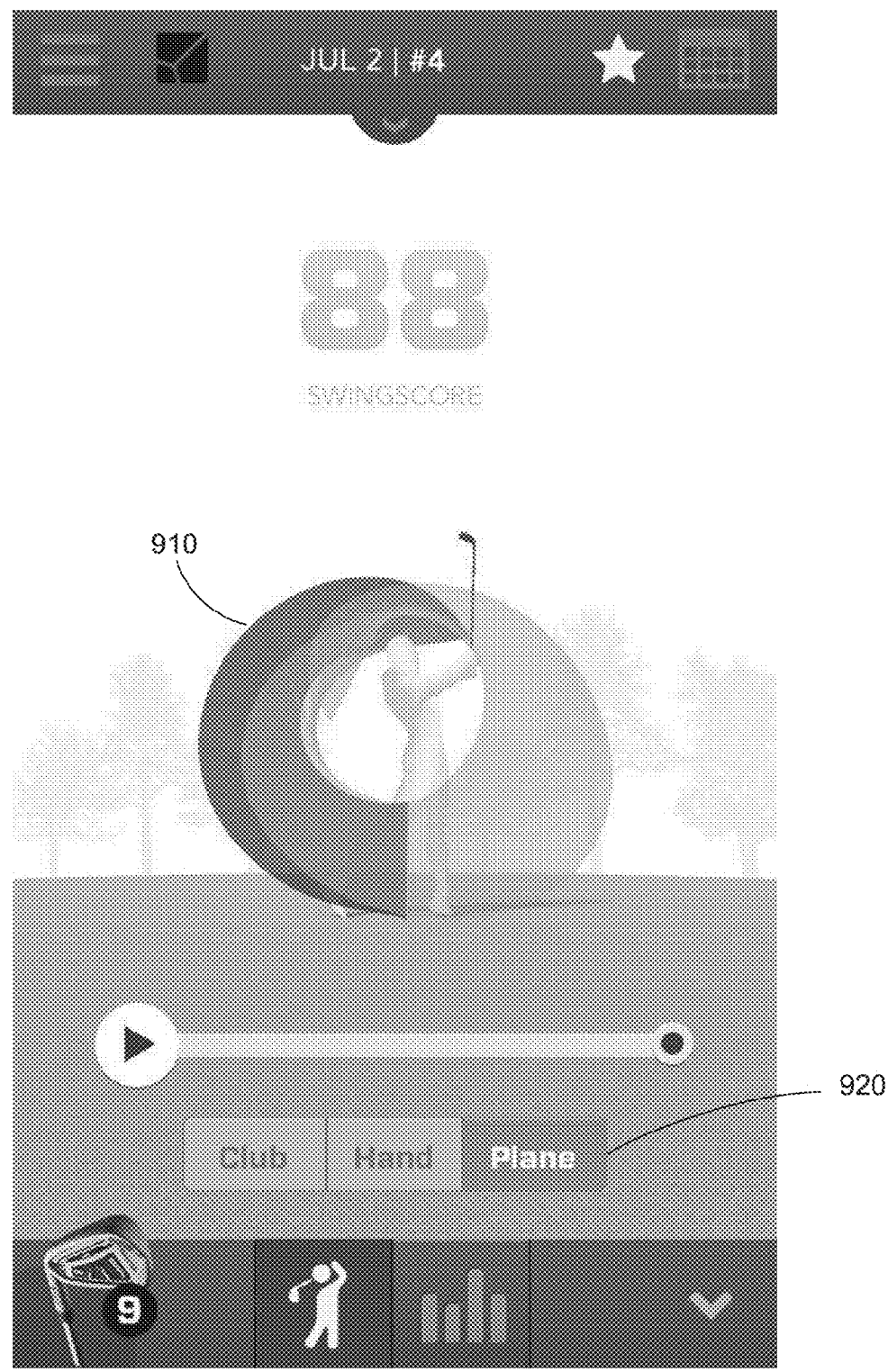
FIG. 9 shows an example of presenting golf club plane aspect of the golf swing illustrated in FIG. 8.

For a golf swing, the recommendation service 140 presents the users various aspects of the swing. FIG. 9 shows an example of presenting golf club plane aspect of the golf swing illustrated in FIG. 8. A club plane measures the relationship between a club head of a downswing and the club head of a backswing, the corresponding distance and location of the club head at different swing positions. The example in FIG. 9 shows the club plane of the golf swing represented by the curved surfaces 910 drawn based on the analysis of the motion parameters related to the club plane 820 of the golf swing.

Figure 10:
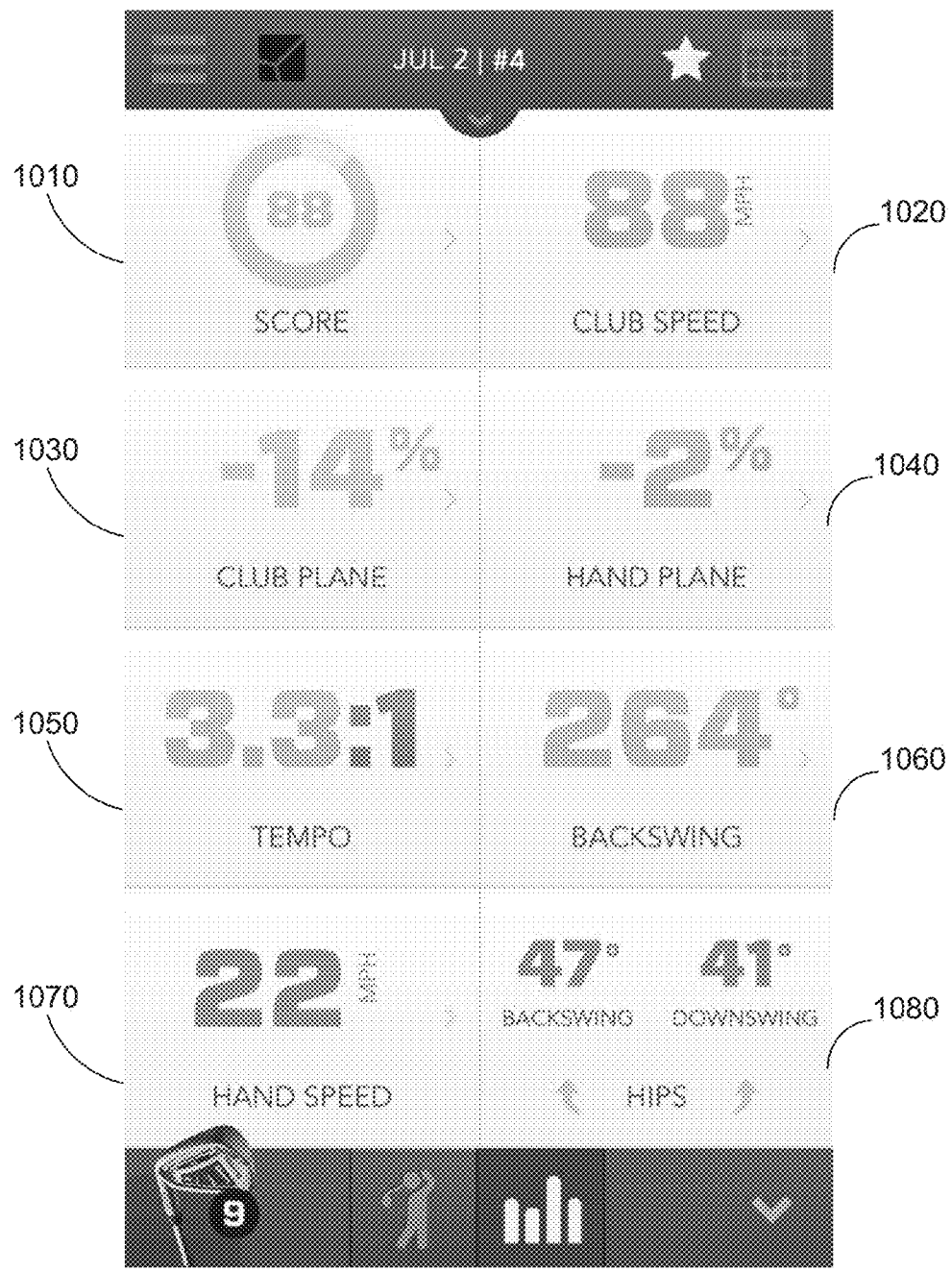
FIG. 10 shows an example of various motion parameters related to a golf swing by a user of the recommendation service.

FIG. 10 shows an example of various motion parameters related to a golf swing by a user of the recommendation service. A golf swing analyzed has seven associated motion parameters, including club speed 1020, club plane 1030, hand plane 1040, tempo 1050, backswing 1060, hand speed 1070 and hips 1080. These seven motion parameters contribute to the calculation of performance scores of various aspects of golf swing. Taking club speed 1020 as an example and assuming that the performance goal of club speed 1020 parameter is 95 mph, and a weighting factor is $1/7$, the contribution of club speed 1020 parameter to the calculation of a user's performance score on a golf swing (e.g., the golf swing shown in FIG. 8 and FIG. 9) is 13.233, which is ($88/95*100*1/7$). For each motion parameter, the player's performance related to that motion parameter is recorded and presented to the player.

Figure 11:
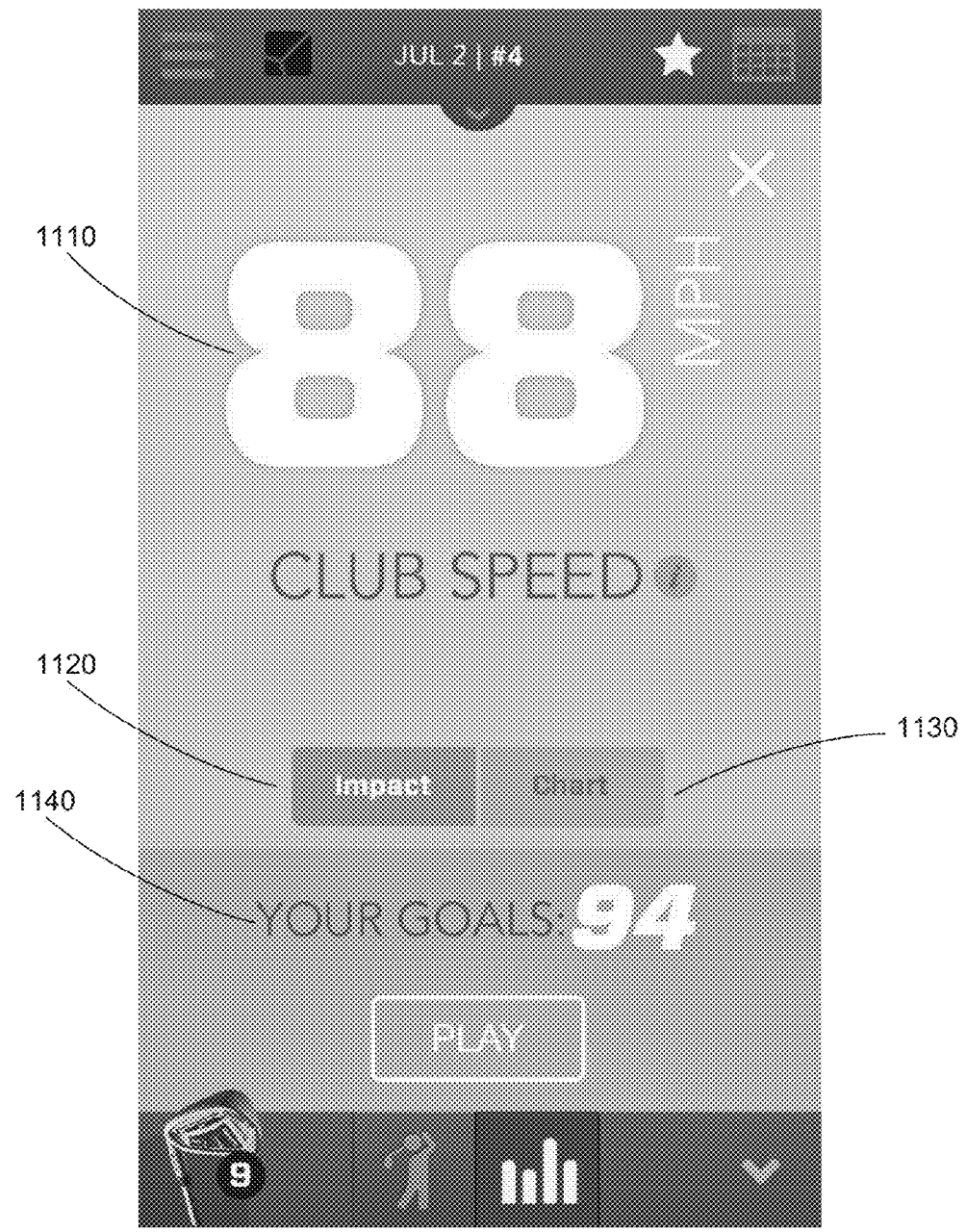
FIG. 11 shows an example of presenting impact of a golf swing on a golf ball and a trend of club speed during the whole process of a golf swing.

FIG. 11 shows an example of presenting impact of a golf swing on a golf ball in terms of club speed and a trend of club speed during the whole process of a golf swing. The presentation illustrated in FIG. 11 shows a performance score 1110 of a player on club speed (e.g., 88 mph) and the player's goal 1140 (e.g., 94 mph). The presentation allows the player to show the impact 1120 in terms of club speed of the club head on a golf ball at various observed time slots. The presentation also shows the player the trend of club speed during the whole process of a golf swing in a form of chart 1130.

Figures 13A, 13B:
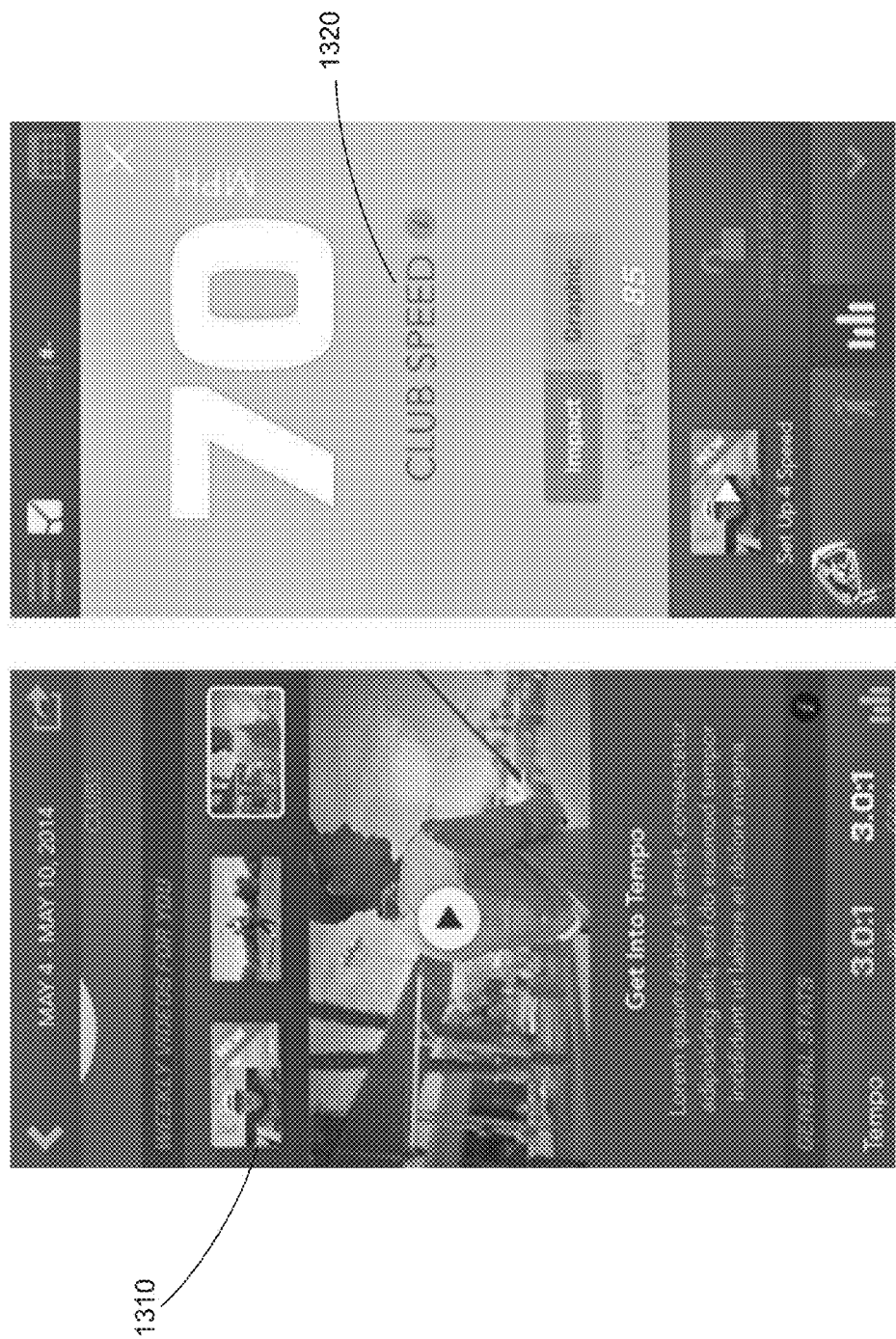
FIG. 13A shows a graphical user interface for presenting three recommended videos for improving performance on club speed.
FIG. 13B shows a graphical user interface for presenting a user's performance on golf club speed.

FIG. 12 illustrates a GUI for users of the recommendation service 140 to customize their golf swinging goals as described above. FIG. 13A shows a GUI for presenting three recommended videos for improving performance on club speed. The recommended videos 1310 are presented to the player weekly and the recommended videos can be delivered to a user via electronic mails (emails), to a user's electronic device that executing an application of the recommendation service or shown on a webpage of the application of the recommendation service on a website hosted by the recommendation service 140.

FIG. 13B shows a GUI for presenting a user's performance on golf club speed 1320. Given the current performance data regarding golf club speed, i.e., 70 mph, of the user and his/her goal to achieve (i.e., 85 mph), the recommendation service 140 ranks the videos on club speed based on their aggregated voting scores, and selects a number of highly relevant videos for the user based on the ranking. The recommended videos are periodically presented to the user, e.g., by weekly as shown in FIG. 13A.

General

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method for recommending a sports video content sample related to a user's sports motion, the method comprising:

selecting a voting method based on motion data of the user's sports motion, the voting method measuring one aspect of the user's sports motion, and the motion data captured by at least one motion data device and the motion data characterized by a plurality of motion parameters;

generating a voting score for each sports video content sample of a plurality of sports video content samples according to the selected voting method, a voting score for a sports video content sample indicating a measurement of performance of a player performing a sports motion captured by the sports video content sample;

ranking the plurality of sports video content samples based on the voting scores associated with the plurality of sports video content samples; and selecting at least one sports video content sample from the plurality of sports video content samples based on the ranking.

2. The computer-implemented method of claim 1, wherein each sports video content sample of the plurality of sports video content samples has an associated sports motion characterized by a plurality of motion parameters.

3. The computer-implemented method of claim 1, wherein the sports motion is a swing of a sports equipment that contacts a ball.

4. The computer-implemented method of claim 3, wherein the swing is one of a swing of a golf club, a swing of a racquet, and a swing of a bat.

5. The computer-implemented method of claim 3, wherein the swing is characterized by a plurality of motion parameters, the motion parameters including a speed of a user's hand holding the sports equipment and a speed of the sports equipment.

6. The computer-implemented method of claim 1, wherein the motion data device is attached to a sports equipment.

7. The computer-implemented method of claim 1, wherein the motion data device is attached to a user's hand holding a sports equipment.

8. The computer-implemented method of claim 1, wherein the motion data device comprises at least one of the following:
 a micro-electromechanical (MEMS) sensor;
 an electromyography (EMG) sensor; and
 a digital camera.

9. The computer-implemented method of claim 1, wherein the plurality of sports video content samples are classified into different classes, each class relating to a different aspect of the sports motion, and the selected sports video content sample having a highest voting score in the aspect of the sports motion measured by the selected voting method.

10. The computer-implemented method of claim 9, wherein the sports motion is a swing of a golf club, and the classes include at least one of the following:
 speed of a head of the golf club;
 swing plane of the golf club;
 hand plane of the swing;
 tempo of the swing;
 backswing of the swing;
 speed of a hand holding the golf club; and
 hip motion.

11. The computer-implemented method of claim 1, wherein at least a portion of the plurality of the sports video content samples are instructional videos illustrating various aspects of the sports motion.

12. The computer-implemented method of claim 1, wherein at least a portion of the plurality of the sports video content samples are videos of professional sports players, coaches or instructors illustrating various aspects of the sports motion.

13. The computer-implemented method of claim 1, further comprising:
 generating a plurality of voting scores for each sports video content sample of the sports video content samples according to a plurality of other voting methods;
 generating an aggregated voting score for each sports video content sample of the sports video content samples by combining the voting scores of the sports video content sample generated according to the plurality of the other voting methods;
 ranking the plurality of sports video content samples based on the aggregated voting scores associated with the sports video content samples; and
 selecting one or more sports video content samples from the sports video content samples based on the ranking.

14. The computer-implemented method of claim 13, wherein the plurality of other voting methods include at least one of the following:
 a measurement of frequency data associated with each sports video content sample;
 a measurement of difference between each sports video content sample and other sports video content samples;
 a measurement of consistency of each sports video content sample with respect to other sports video content samples;
 a measurement of user ratings of each sports video content sample; and
 a measurement of duplication of each sports video content sample.

15. The computer-implemented method of claim 13, wherein generating an aggregated voting score for each sports video content sample of the sports video content samples comprises:
 applying scaling factors associated with the plurality of other voting methods, the scaling factor associated with a voting method indicating a relative importance of the voting method, wherein the scaling factors are configurable for different sports motions.

16. A non-transitory computer readable medium storing executable computer program instructions for recommending a sports video content sample related to a user's sports motion, the computer program instructions comprising instructions for:
 selecting a voting method based on motion data of the user's sports motion, the voting method measuring one aspect of the user's sports motion, and the motion data captured by at least one motion data device and the motion data characterized by a plurality of motion parameters;
 generating a voting score for each sports video content sample of a plurality of sports video content samples according to the selected voting method, a voting score for a sports video content sample indicating a measurement of performance of a player performing a sports motion captured by the sports video content sample;
 ranking the plurality of sports video content samples based on the voting scores associated with the plurality of sports video content samples; and
 selecting at least one sports video content sample from the plurality of sports video content samples based on the ranking.

17. The computer-readable storage medium of claim 16, wherein each sports video content sample of the plurality of sports video content samples has an associated sports motion characterized by a plurality of motion parameters.

18. The computer-readable storage medium of claim 16, wherein the sports motion is a swing of a sports equipment that contacts a ball, and the swing is one of a swing of a golf club, a swing of a racquet, and a swing of a bat.

19. The computer-readable storage medium of claim 18, wherein the swing is characterized by a plurality of motion parameters, the motion parameters including a speed of a user's hand holding the sports equipment and a speed of the sports equipment.

20. The computer-readable storage medium of claim 16, wherein the motion data device is attached to a sports equipment.

21. The computer-readable storage medium of claim 16, wherein the plurality of sports video content samples are classified into different classes, each class relating to a different aspect of the sports motion, and the selected sports video content sample having a highest voting score in the aspect of the sports motion measured by the selected voting method.

22. The computer-readable storage medium of claim 21, wherein the sports motion is a swing of a golf club, and the classes include at least one of the following:
   speed of a head of the golf club;
   swing plane of the golf club;
   hand plane of the swing;
   tempo of the swing;
   backswing of the swing;
   speed of a hand holding the golf club; and
   hips motion.

23. The computer-readable storage medium of claim 16, wherein at least a portion of the plurality of the sports video content samples are instructional videos illustrating various aspects of the sports motion.

24. The computer-readable storage medium of claim 16, wherein at least a portion of the plurality of the sports video content samples are videos of professional sports players, coaches or instructors illustrating various aspects of the sports motion.

25. The computer-readable storage medium of claim 16, further comprising computer program instructions for:
   generating a plurality of voting scores for each sports video content sample of the sports video content samples according to a plurality of other voting methods;
   generating an aggregated voting score for each sports video content sample of the sports video content samples by combining the voting scores of the sports video content sample generated according to the plurality of the other voting methods;
   ranking the plurality of sports video content samples based on the aggregated voting scores associated with the sports video content samples; and
   selecting at least one sports video content sample from the plurality of sports video content samples based on the ranking.

26. The computer-readable storage medium of claim 25, wherein the plurality of other voting methods include at least one of the following:
   a measurement of frequency data associated with each sports video content sample;
   a measurement of difference between each sports video content sample and other sports video content samples;
   a measurement of consistency of each sports video content sample with respect to other sports video content samples;
   a measurement of user ratings of each sports video content sample; and
   a measurement of duplication of each sports video content sample.

27. The computer-readable storage medium of claim 25, wherein the computer program instructions for generating an aggregated voting score for each sports video content sample of the sports video content samples comprise instructions for:
   applying scaling factors associated with the plurality of other voting methods, the scaling factor associated with a voting method indicating a relative importance of the voting method, wherein the scaling factors are configurable for different sports motions.

28. A computer-implemented method for selecting sports video content samples related to a user's sports motion, the method comprising:
   receiving a plurality of sports video content samples and a plurality of voting methods, each sports video content sample having a sports motion defined by one or more motion parameters;
   applying the plurality of voting methods to each sports video content sample of the plurality of sports video content samples, a voting method applied to a sports video content sample measuring a player's performance of performing the sports motion of the sports video content sample;
   generating a plurality of voting scores for each sports video content sample of the sports video content samples according to the plurality of voting methods, a voting score of a sports video content sample generated according to a voting method indicating a measurement of the player's performance measured by the voting method;
   selecting a voting method from the plurality of voting methods based on motion data of the user's sports motion captured by at least one motion data device, the motion data characterized by a plurality of motion parameters, and the selected voting method measuring one aspect of the user's sports motion;
   ranking the plurality of sports video content samples based on the voting scores of the plurality of sports video content samples generated according to the selected voting method; and
   selecting one or more sports video content samples for the selected voting method based on the ranking.

29. The method of claim 28, further comprising:
   selecting another voting method based on one or more motion parameters describing another aspect of the user's sports motion;
   generating a voting score for each sports video content sample of the sports video content samples according to the selected another voting method;
   ranking the plurality of sports video content samples based on the voting scores associated with the sports video content samples generated according to the selected another voting method; and
   selecting one or more sports video content samples from the sports video content samples based on the ranking.

30. The method of claim 28, further comprising:
   generating a voting score for a sports video content sample of the plurality of sports video content samples based on a shifted standard deviation of the sports content sample with respect to all other sports video content samples having a same type of sports motion as the sports video content sample.

* * * * *